US00PP35208P2

(12) United States Plant Patent
Kolster et al.

(10) Patent No.: US PP35,208 P2
(45) Date of Patent: Jun. 6, 2023

(54) ***HYDRANGEA* PLANT NAMED 'HOKOMAROUGE'**

(50) Latin Name: *Hydrangea macrophylla*
Varietal Denomination: Hokomarouge

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOESTER HOLDING BV, Boskoop (NL), part interest; HORTEVE BREEDING BV, Aalsmeer (NL), part interest ( * ) Notice: Subject to any disclaimer, the term of this patent is extended or adjusted under 35 U.S.C. 154(b) by 0 days.

(21) Appl. No.: 18/082,981

(22) Filed: Dec. 16, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* plant named 'Hokomarouge' that is characterized by its good growing habit, its very floriferous plant habit, its densely branched plant habit, its inflorescences that mature from green to deep pink in color, and its suitability for use as a potted plant.

2 Drawing Sheets

Botanical classification: *Hydrangea macrophylla.*
Varietal denomination: 'Hokomarouge'.

BACKGROUND OF THE INVENTION

The present invention relates to a new and distinct cultivar of *Hydrangea macrophylla* and will be referred to hereafter by its cultivar name, 'Hokomarouge'. 'Hokomarouge' represents a new bigleaf *Hydrangea*, a perennial shrub grown for landscape use and as a potted plant.

'Hokomarouge' was derived from an ongoing controlled breeding program directed by the Inventors. A goal of the breeding program was to develop a new cultivar of *Hydrangea* with unique flower colors and dense branching plant habit with suitability for growing as a potted plant.

'Hokomarouge' arose from a controlled cross made by the Inventors in Boskoop, The Netherlands in February of 2013 between *Hydrangea* 'Jong-1' (not patented) as the female parent and *Hydrangea* '11-026-04' (not patented) as the male parent. 'Hokomarouge' was selected as a single unique plant from amongst the resulting seedlings in May of 2015.

Asexual propagation of the new cultivar was first accomplished by stem cuttings by one of the Inventors in July of 2015 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomarouge' as a unique cultivar of *Hydrangea macrophylla.*

1. 'Hokomarouge' exhibits a good growing habit.
2. 'Hokomarouge' exhibits a very floriferous plant habit.

3. 'Hokomarouge' exhibits a densely branched plant habit.
4. 'Hokomarouge' exhibits inflorescences that mature from green to deep pink in color.
5. 'Hokomarouge' exhibits suitability for use as a potted plant.

The female parent of 'Hokomarouge' differs from 'Hokomarouge' in having inflorescences with sterile sepals that are more red in color, fewer branches, and a less floriferous plant habit. The male parent of 'Hokomarouge' differs from 'Hokomarouge' in having inflorescences that are larger in size and white-pink in color, fewer branches, and a less floriferous plant habit. 'Hokomarouge' can be most closely compared to the *Hydrangea macrophylla* cultivars 'Kolmapiru' (not patented) and 'Hortmadace' (U.S. Plant Pat. No. 28,084). 'Kolmapiru' is similar to 'Hokomarouge' in having inflorescences that are similar in color and in being suitable for use as a potted plant. 'Kolmapiru' differs from 'Hokomarouge' in having branches that are longer but fewer in number, inflorescences with less green on the sepals, and leaves that are dark green in color. 'Hortmadace' is similar to 'Hokomarouge' in being suitable as a potted plant, having hard inflorescences that are pink in color, and being densely branched. 'Hortmadace' differs from 'Hokomarouge' in having fewer branches, and inflorescences that are softer in texture with sterile flower sepals that are all pink in color.

STATEMENT REGARDING PRIOR DISCLOSURES BY THE INVENTOR

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the effective filing date. Disclosures include website listings by Nursery Mag, Plants Nouveau, and Kamps *Hydrangea*.

BRIEF DESCRIPTION OF THE DRAWINGS

The accompanying color photographs illustrate the overall appearance and distinct characteristics of the new *Hydrangea*. The photographs were taken of a two-year-old plant of 'Hokomarouge' as grown in a greenhouse in a 2-gallon container in Abbotsford, B.C., Canada.

The photograph in FIG. 1 provides a side view of 'Hokomarouge' in bloom.

Figure 1:
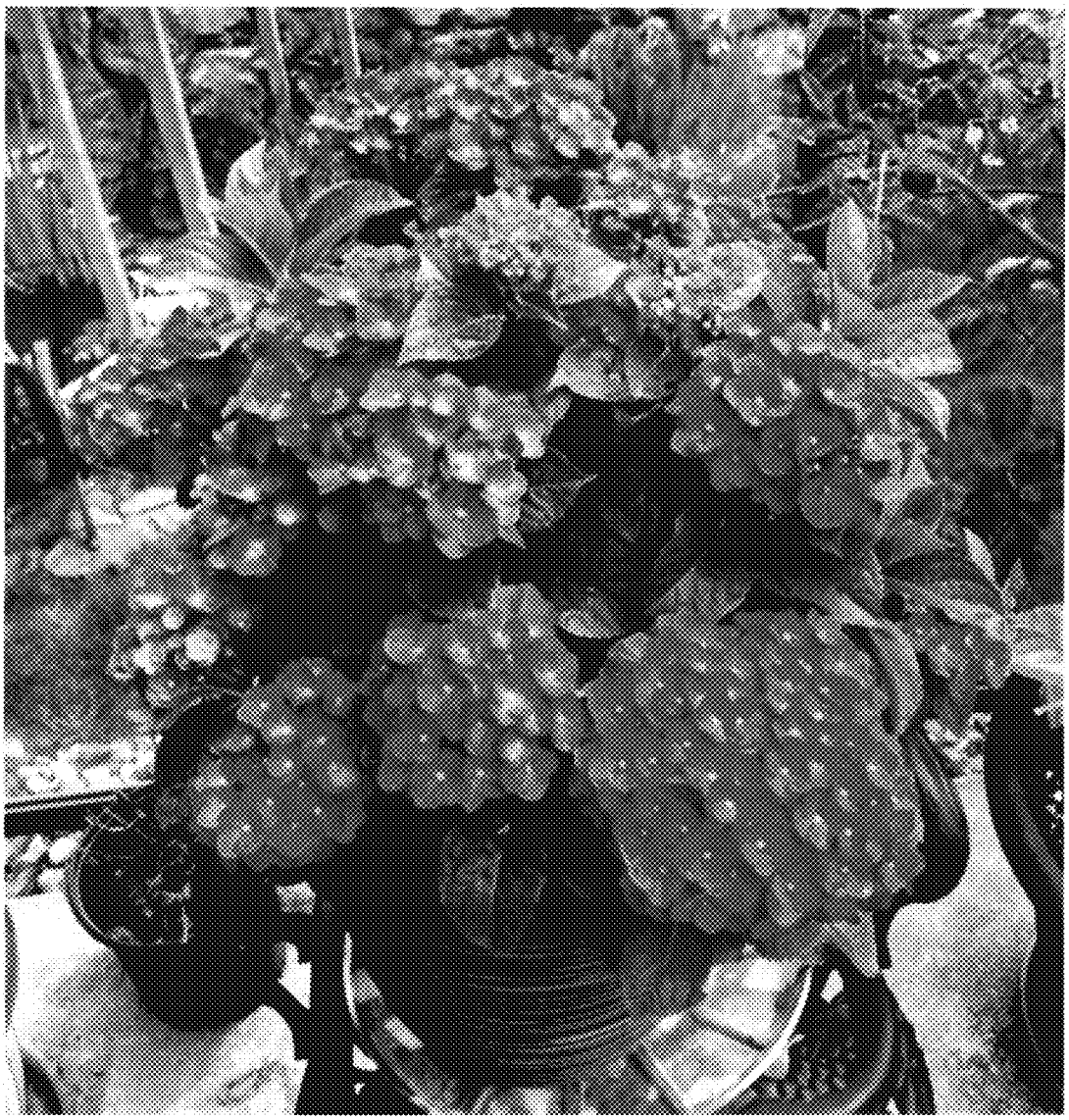
Figure 2:
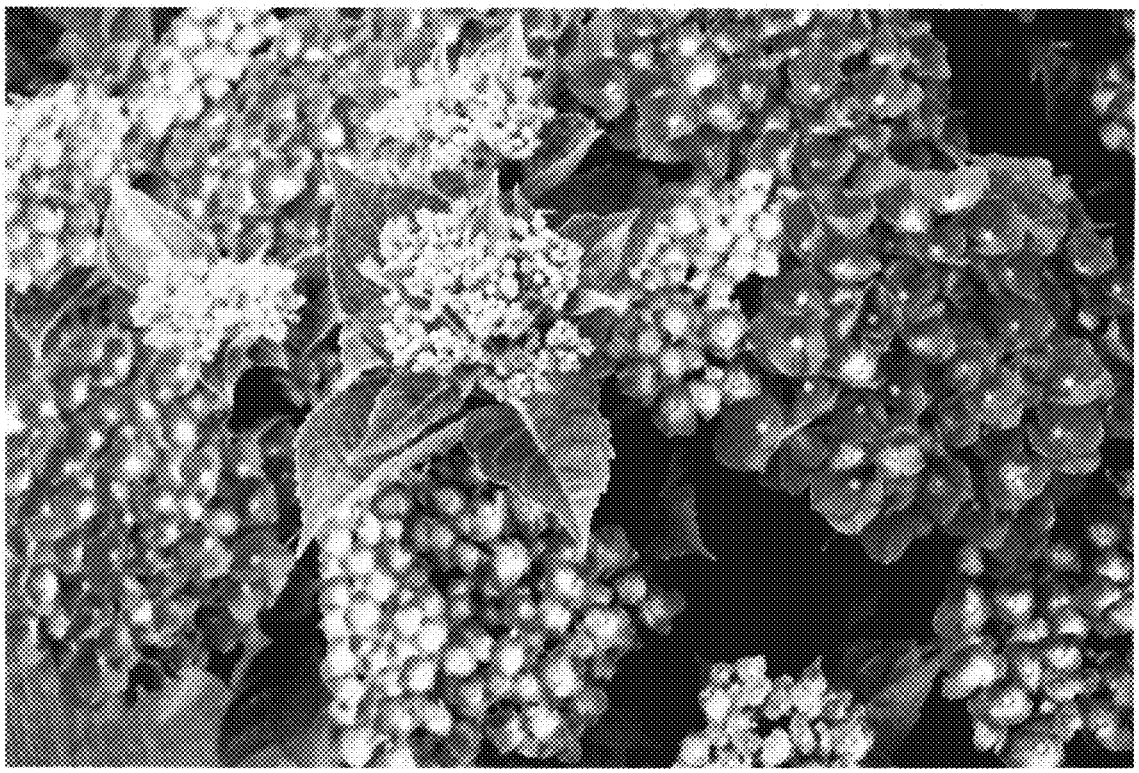

The photograph in FIG. 2 provides a close-up view of the changing colors of the inflorescences of 'Hokomarouge'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of one-year-old plants of 'Hokomarouge' as grown in a greenhouse in 6-inch containers in Vineland, Ontario, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General Description:

- *Blooming period*.—Late spring to late summer with flowers showy at least for 2 months in The Netherlands.
- *Plant type*.—Deciduous shrub, mophead type *Hydrangea*.
- *Plant habit*.—Upright, compact.
- *Height and spread*.—An average of 28 cm in height and 38 cm in spread, 80 cm in height and width as a 3-year-old plant grown in the landscape.
- *Hardiness*.—At least in U.S.D.A. Zones 5 to 9.
- *Diseases and pests*.—No susceptibility and resistance to diseases or pests has been observed.
- *Root description*.—Fine and fibrous, 161C in color.
- *Propagation*.—Stem cuttings.
- *Root development*.—An average of 6 weeks for root initiation with a young rooted plant produced in an average of 18 weeks.
- *Growth rate and vigor*.—Moderate.

Branch description:

- *Branch shape*.—Rounded.
- *Branch strength*.—Strong.
- *Branch color*.—Young; 145A, mature; 144A, older woody branches; 200B, old bark; 200A, 200B, and 177B.
- *Branch size*.—An average of 20 cm in length (excluding inflorescence) and 7 mm in diameter.
- *Branch surface*.—Young and mature; glossy, glabrous, branches are sparsely covered with lenticels; oval in shape, average of 7 per 1 cm diameter, average of 1 mm in length, 0.2 mm in width, 200A in color, older woody branches; matte with a sheen, glabrous, old bark; exfoliating, matte, dry.
- *Branch aspect*.—Upright to slightly outward.
- *Internode length*.—An average of 2 cm.
- *Branching*.—Freely branching; 12 main branches, 4 to 6 lateral branches per main branch.

Foliage description:

- *Leaf shape*.—Broad ovate.
- *Leaf arrangement*.—Opposite.
- *Leaf division*.—Simple.
- *Leaf base*.—Short attenuate.
- *Leaf apex*.—Short apiculate.
- *Leaf margins*.—Coarsely serrate.
- *Leaf venation*.—Pinnate, color; upper and lower surface 145A.
- *Leaf size*.—An average of 7.5 cm in length and 5 cm in width.
- *Leaf attachment*.—Petiolate.
- *Leaf number*.—An average of 14 per lateral stem.
- *Leaf surface*.—Upper surface; glabrous, matte with a slight sheen, lower surface glabrous, matte.
- *Leaf color*.—Young and mature foliage; upper surface 139A, lower surface 138B.
- *Petioles*.—An average of 1.2 cm in length and 2 mm in diameter, upper and lower surface color 145A, both surfaces are smooth and slightly glossy.

Inflorescence description:

- *Inflorescence type*.—Terminal panicle, flattened mophead comprised of sterile flowers above fertile flowers.
- *Lastingness of inflorescence*.—Sterile flowers; persistent for an average of 6 weeks, fertile flowers; self-cleaning, an average of 5 days.
- *Inflorescence number*.—One per lateral stem.
- *Inflorescence size*.—An average of 9 cm in height and 13 cm in diameter.
- *Flower number*.—An average of 50 sterile flowers and 10 fertile flowers per panicle.
- *Flower fragrance*.—None.
- *Flower aspect*.—Upright to outward.
- *Flower size*.—Sterile flowers; an average of 3 cm in diameter and 1 cm in depth, fertile flowers; an average of 1 cm in diameter and 3 mm in depth.
- *Flower type*.—Rotate.
- *Flower buds*.—Sterile flowers; an average of 8 mm in length and 4 mm in diameter, obovate in shape, 144B, fertile flowers; an average of 2 mm in length and 1 mm in diameter, obovate in shape, color; 144B.
- *Peduncles*.—Strong, round in shape, an average of 2 cm in length and 2 mm in width, 147B in color, surface slightly glossy and moderately covered with thin pubescence too small to measure.
- *Pedicels*.—Sterile flowers; held primarily at an average angle of 30°, an average of 2 cm in length and 2 mm in diameter, moderately strong strength, color; 145D, flushed with 70D, occasional thin lines of N79B, surface matte and glabrous, fertile flowers; held at an average angle of 20° from vertical, an average of 3 mm in length and 1 mm in diameter, moderate strength, 70D in color, matte and glabrous surface.
- *Petals*.—Sterile flowers; an average of 5, rotate, cruciform in arrangement, acute apex, cuneate base, entire margins, ovate to moderately concave in shape, average of 3 mm in length and 2 mm in width, both surfaces; smooth, glabrous and matte, color;

when opening upper and lower surface 157A, when fully open upper and lower surface a blend of 73A, 73B, and 73C, fertile flowers; an average 5, rotate in arrangement, ovate and concave in shape, entire margin, acute apex, cuneate base, an average of 2 mm in length and 1 mm in width, upper and lower surface glabrous and matte, color; when opening upper and lower surface 157A and 145B, when fully open upper and lower surface; 68C.

*Sepals*.—Sterile flowers; 4, rotate, broadly and bluntly acute apex with an emarginate outer tip, broadly cuneate base, entire margins, reniform to nearly deltoid in shape, an average of 2 cm in length and width, upper and lower surface glabrous and matte, color; when opening upper surface 144B, flushed with 61A and 61B, veins 69A, when opening lower surface 145C, when fully open upper surface NN74B, hints of N148A, when fully open lower surface a blend of 75B and 75D, upper and lower surface fading to 77A, fertile flowers; dropped when maturing.

Reproductive organs:

*Gynoecium*.—Sterile flowers; 3 pistils, an average of 0.5 mm in length, stigma; club-shaped and 158A in color, style; 0.3 mm in length, color; 158A, top (under the stigma) NN78A, ovary; oval, superior, is 157A in color, fertile flowers; an average of 3 pistils, an average of 1 mm in length, stigma; club-shaped and 158A in color, style; 0.5 mm in length and NN78A in color, ovary is 158A in color.

*Androecium*.—Sterile flowers; an average of 8 stamens, filaments; an average of 1 mm in length and NN155D in color, anthers; broad oblong in shape, an average of 0.75 mm in length and color; 155D, center 145A, pollen; none observed, fertile flowers; an average of 10 stamens, filaments; an average of 1 mm in length and 155B in color, anthers; broad oblong in shape, an average of 0.5 mm in length and 155D in color, pollen; none observed.

*Fruit and seed*.—None observed to date.

It is claimed:

1. A new and distinct cultivar of *Hydrangea* plant named 'Hokomarouge' substantially as herein illustrated and described.

* * * * *